US010070972B2

(12) United States Patent
Maher et al.

(10) Patent No.: US 10,070,972 B2
(45) Date of Patent: Sep. 11, 2018

(54) SYSTEM AND METHOD FOR INTRAOPERATIVE JOINT CONTACT MECHANICS MEASUREMENT

(71) Applicant: Hospital for Special Surgery, New York, NY (US)

(72) Inventors: Suzanne Maher, Highland Lakes, NJ (US); Scott Rodeo, New York, NY (US); Russell Warren, Greenwich, CT (US); Hongsheng Wang, Elmhurst, NY (US); Mario Lustri, Brooklyn, NY (US)

(73) Assignee: Hospital for Special Surgery, New York, NY (US)

( * ) Notice: Subject to any disclaimer, the term of this patent is extended or adjusted under 35 U.S.C. 154(b) by 275 days.

(21) Appl. No.: 14/875,230

(22) Filed: Oct. 5, 2015

(65) Prior Publication Data
US 2016/0100905 A1    Apr. 14, 2016

Related U.S. Application Data

(60) Provisional application No. 62/059,263, filed on Oct. 3, 2014.

(51) Int. Cl.
| | | |
|---|---|---|
| *A61F 2/46* | (2006.01) | |
| *A61B 19/00* | (2006.01) | |
| *A61B 5/00* | (2006.01) | |
| *A61B 17/00* | (2006.01) | |
| *A61F 2/38* | (2006.01) | |

(52) U.S. Cl.
CPC .......... *A61F 2/4657* (2013.01); *A61B 5/4528* (2013.01); *A61B 5/4585* (2013.01); *A61B 5/4884* (2013.01); *A61B 5/6867* (2013.01); *A61B 5/743* (2013.01); *A61B 19/46* (2013.01); *A61B 5/4576* (2013.01); *A61B 2017/00022* (2013.01); *A61B 2017/00867* (2013.01); *A61B 2019/465* (2013.01); *A61B 2019/466* (2013.01); *A61B 2505/05* (2013.01); *A61B 2562/0247* (2013.01); *A61B 2562/0252* (2013.01);
(Continued)

(58) Field of Classification Search
CPC ... A61B 5/4585; A61B 5/4528; A61B 5/4533; A61B 5/4538; A61F 2002/4666
See application file for complete search history.

(56) References Cited

U.S. PATENT DOCUMENTS

| | | |
|---|---|---|
| 7,139,601 B2 | 11/2006 | Bucholz et al. |
| 7,366,562 B2 | 4/2008 | Dukesherer et al. |
| | (Continued) | |

OTHER PUBLICATIONS

Gelber, Allan C., et al. "Joint injury in young adults and risk for subsequent knee and hip osteoarthritis." Annals of internal medicine 133.5 (2000): 321-328.
(Continued)

*Primary Examiner* — Andrew Yang
(74) *Attorney, Agent, or Firm* — Kim Winston LLP

(57) ABSTRACT

A method for intraoperatively measuring joint contact mechanics of a patient's joint is provided. The method includes inserting a sensor between first and second bones of a joint. Then a predetermined force is applied to one of the first and second bones. Afterwards, contact mechanics such as, contact stresses, contact areas and/or forces are measured between the first and second bones in response to the applied predetermined force.

19 Claims, 13 Drawing Sheets

(52) U.S. Cl.
CPC ..... *A61F 2/3872* (2013.01); *A61F 2002/4666* (2013.01); *A61F 2002/4667* (2013.01)

(56) References Cited

U.S. PATENT DOCUMENTS

| | | | |
|---|---|---|---|
| 7,522,948 B2* | 4/2009 | Chin | A61B 5/14552 |
| | | | 600/310 |
| 7,751,865 B2 | 7/2010 | Jascob et al. | |
| 8,555,633 B2 | 10/2013 | Alexander et al. | |
| 8,623,030 B2 | 1/2014 | Bonutti | |
| 8,644,907 B2 | 2/2014 | Hartmann et al. | |
| 9,082,319 B2 | 7/2015 | Shimada et al. | |
| 2004/0073137 A1* | 4/2004 | Lloyd | A61B 3/16 |
| | | | 600/561 |
| 2010/0249658 A1* | 9/2010 | Sherman | A61B 5/103 |
| | | | 600/587 |

OTHER PUBLICATIONS

Lohmander, L. S., et al. "High prevalence of knee osteoarthritis, pain, and functional limitations in female soccer players twelve years after anterior cruciate ligament injury." Arthritis & Rheumatism 50.10 (2004): 3145-3152.

Verdonk, Peter CM, et al. "Meniscal allograft transplantation: long-term clinical results with radiological and magnetic resonance imaging correlations." Knee Surgery, Sports Traumatology, Arthroscopy 14.8 (2006): 694-706.

Lohmander, L. Stefan, et al. "The long-term consequence of anterior cruciate ligament and meniscus injuries osteoarthritis." The American journal of sports medicine 35.10 (2007): 1756-1769.

Vundelinckx, Bart, Johan Bellemans, and Johan Vanlauwe. "Arthroscopically Assisted Meniscal Allograft Transplantation in the Knee A Medium-Term Subjective, Clinical, and Radiographical Outcome Evaluation." The American journal of sports medicine 38.11 (2010): 2240-2247.

* cited by examiner

Menisectomy

Meniscal Allograft Transplantation

Stress (MPa)

0          2

Stress (MPa)

0          2

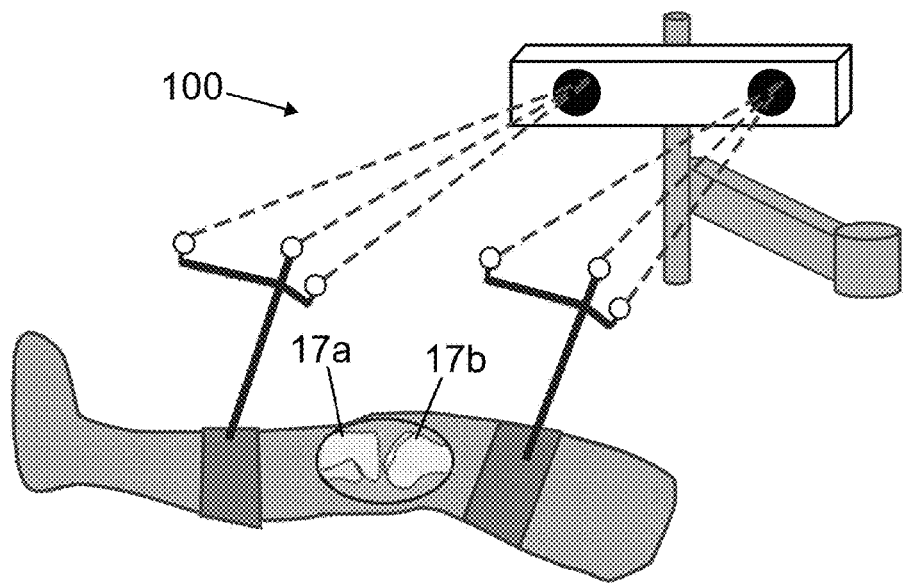
FIG. 11
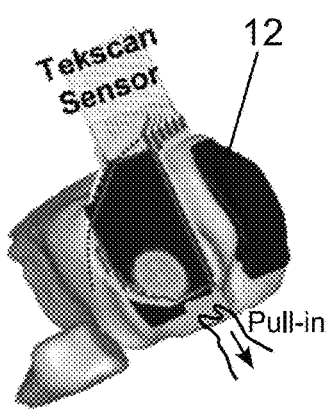 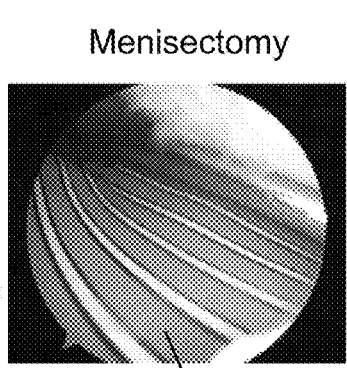 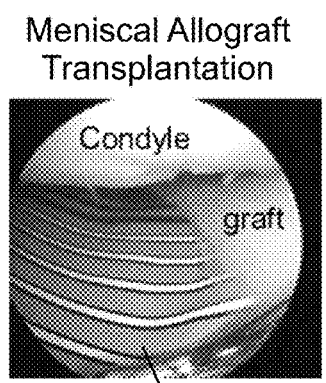
FIG. 12A  FIG. 12B  FIG. 12C

SYSTEM AND METHOD FOR INTRAOPERATIVE JOINT CONTACT MECHANICS MEASUREMENT

CROSS REFERENCE TO RELATED APPLICATIONS

The present application claims the benefit of U.S. Provisional Patent Application No. 62/059,263 filed Oct. 3, 2014 entitled "INTRA-OPERATIVE JOINT CONTACT STRESS MEASUREMENT UNDER KNOWN LOADS," the entire disclosure of which is hereby incorporated by reference herein for all purposes.

BACKGROUND OF THE INVENTION

The present invention relates generally to the field of orthopedics and study and treatment of joints. In particular, the present invention relates to a system and method for intraoperative joint contact mechanics measurement of a patient.

Injuries to the joints of the musculoskeletal system are common either because of sports related activities, regular wear and tear, or aging. When rehabilitation fails to alleviate symptoms, or when the injury itself significantly affects the performance or activities of daily living, surgery is performed to repair or replace the damaged tissue of the joint. The short- to medium-term goals of surgery are to relieve pain and restore the native functions of the joint.

The effect of injury on the long-term health of joints, such as the knee, hip and shoulder, has been documented; with most injuries leading to increased risk of the development of osteoarthritis (OA). According to a prospective study of 1321 participants with median follow-up of 36 years, young adults with joint injuries are at considerably increased life-time risk for osteoarthritis (relative risk of 5.17 for knee and 3.50 for hip, respectively) and should be targeted in the primary prevention of osteoarthritis. (Gelber, A. C., M. C. Hochberg, L. A. Mead, N. Y. Wang, F. M. Wigley and M. J. Klag (2000). "Joint injury in young adults and risk for subsequent knee and hip osteoarthritis." Ann Intern Med 133(5): 321-328.) Thus, the long-term goal of surgical treatment is to protect the knee joint from developing OA. Unfortunately, this goal has not been achieved by current surgical methods.

With respect to the knee joint, more than 50% of patients who have received anterior cruciate ligament (ACL) reconstruction develop advanced OA within 10 years of surgery. (Lohmander, L. S., A. Ostenberg, M. Englund and H. Roos (2004). "High prevalence of knee osteoarthritis, pain, and functional limitations in female soccer players twelve years after anterior cruciate ligament injury"; Arthritis Rheum 50(10): 3145-3152, and Lohmander, L. S., P. M. Englund, L. L. Dahl and E. M. Roos (2007). "The long-term consequence of anterior cruciate ligament and meniscus injuries: osteoarthritis." Am J Sports Med 35(10): 1756-1769.)

For meniscal injuries there is an incidence of 59% radiographic joint space narrowing and 65% continued joint degeneration in patients 10 years after meniscal allograft transplantation (MAT) surgery. (Verdonk, P. C., K. L. Verstraete, K. F. Almqvist, K. De Cuyper, E. M. Veys, G. Verbruggen and R. Verdonk (2006). "Meniscal allograft transplantation: long-term clinical results with radiological and magnetic resonance imaging correlations." Knee Surg Sports Traumatol Arthrosc 14(8): 694-706.) Similar results were also reported in another study where 42% of the patients had significant increase in osteoarthritis scores at 10 years of MAT. Given the aging population and the socio-economic burden of OA, there are ongoing investigations to understand the development of the disease after injury—so called, post-traumatic OA. (Vundelinckx, B., J. Bellemans and J. Vanlauwe (2010). "Arthroscopically assisted meniscal allograft transplantation in the knee: a medium-term subjective, clinical, and radiographical outcome evaluation." Am J Sports Med 38(11): 2240-2247.)

Current methods used to evaluate an injured joint include feedback from the patient (pain scores, description of degree of pain and location), physical examination (range of motion, laxity tests) and radiological assessment (MRI, CT). Further, surgical techniques used to treat injured joints are intended to restore the ability of the joint to mechanically function. For example, mechanical function can be recaptured by restoring stability so that the joint can carry loads in a stable way through the necessary range of motion for daily activities (ACL reconstruction, tendon transfers, rotator cuff repair), or locally repairing the site of damaged tissue so that it can carry or distribute joint loads (articular cartilage repair, meniscal repair).

Assessing patient outcome, however, is difficult. Pain levels and return to daily activities are subjectively scored by the patient in a post-operative environment. Imaging is also used to assess the durability of the repair and the overall status of the joint. But, by the time these measures are made, significant time e.g., 6 weeks to 3 months have passed.

Thus, there is still a need to address the foregoing limitations of conventional surgery. Such a need is satisfied by the present invention.

BRIEF SUMMARY OF THE INVENTION

In accordance with a preferred embodiment, the present invention provides a method for intraoperatively measuring joint contact mechanics of a patient's joint. The method includes inserting a sensor between first and second bones of a joint, applying a predetermined force to one of the first and second bones, and measuring contact mechanics between the first and second bones in response to the applied predetermined force. The method further comprising tracking movement of the first and second bones in response to the applied predetermined force using a surgical navigation system. Furthermore, the method includes mitigating joint interaction about areas of measured contact stresses or contact areas, and developing a contact stress map based on the measured contact stresses. The contact mechanics include contact area, contact stress, forces or moments.

The predetermined force can be a linear force, a torque or a moment, or combinations thereof. The step of applying a predetermined force comprises rotating the joint throughout a range of motion. Further, the step of applying a predetermined force comprises displacing or translating one of the first and second bones relative to the other of the first and second bones.

The measuring step comprises intraoperatively measuring a plurality of contact mechanics at various times. Further, the measuring step includes measuring the location of a contact area, a contact stress, forces or moments between the first and second bones in response to the applied predetermined force.

The mitigating step comprises applying scaffolds, sutures, biological augments, or tissue resection to one of the first and second bones. Further, the mitigating step comprises replacing or resurfacing the joint with an orthopedic implant.

The inserting step comprises suturing the sensor to soft tissue adjacent one of the first and second bones. Further, the inserting step comprises inserting the sensor between at least one of a tendon, a cartilage, and a meniscus, and the first bone. Furthermore, the inserting step comprises rolling the sensor into a rolled configuration, inserting the rolled sensor into a cannula, inserting the cannula into the joint, and unrolling the sensor within the joint.

In accordance with another preferred embodiment, the present invention provides a system for intraoperatively measuring joint contact mechanics of a patient's joint. The system includes a sensor for measuring joint contact stresses between first and second bones of the joint, a load cell for measuring forces applied to one of the first and second bones, and a computer operatively in communication with the sensor and configured to record contact mechanics measured by the sensor upon application of forces to one of the first and second bones. The sensor includes sutures for securing to soft tissue adjacent one of the first and second bones. Further, the sensor can comprise shape memory alloy. The system further includes a surgical navigation system configured to track the first and second bones upon application of forces to the first and second bones.

In accordance with an aspect, the present invention provides an intraoperative method to allow for joint contact mechanics (e.g., the stresses, areas and forces acting across the surface of a joint) to be measured at various stages throughout the surgery. The method involves several key steps.

An electronic sensor capable of measuring contact mechanics is sterilized, conditioned, equilibrated, and calibrated as per manufacturer's guidelines prior to the time of surgery. The sensor is pre-loaded with sutures, and drawn into the joint through an arthrotomy. An instrumented boot is placed on a site distal to the joint being operated upon. Both the instrumented boot and the electronic sensors are connected to a PC/laptop, to allow pre-loaded programs to record forces through the boot and contact mechanics as recorded by the sensor are visualized by the operating room team, and stored on the computer for subsequent analysis. The boot and the electronic sensors can be removed and replaced at multiple times during the surgery, so that data can be recorded at various stages of the procedure.

BRIEF DESCRIPTION OF THE SEVERAL VIEWS OF THE DRAWINGS

The foregoing summary, as well as the following detailed description of the preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings:

FIG. 11 is a schematic partial perspective view of a surgical navigation system applicable to the preferred embodiments of the present invention;

FIG. 12A is an illustration of a sensor of the system for intraoperatively measuring joint contact mechanics applied to a tibia;

FIGS. 12B and 12C are arthroscopic photos of a sensor positioned within a knee joint of a patient;

DETAILED DESCRIPTION OF THE INVENTION

Figure 1:
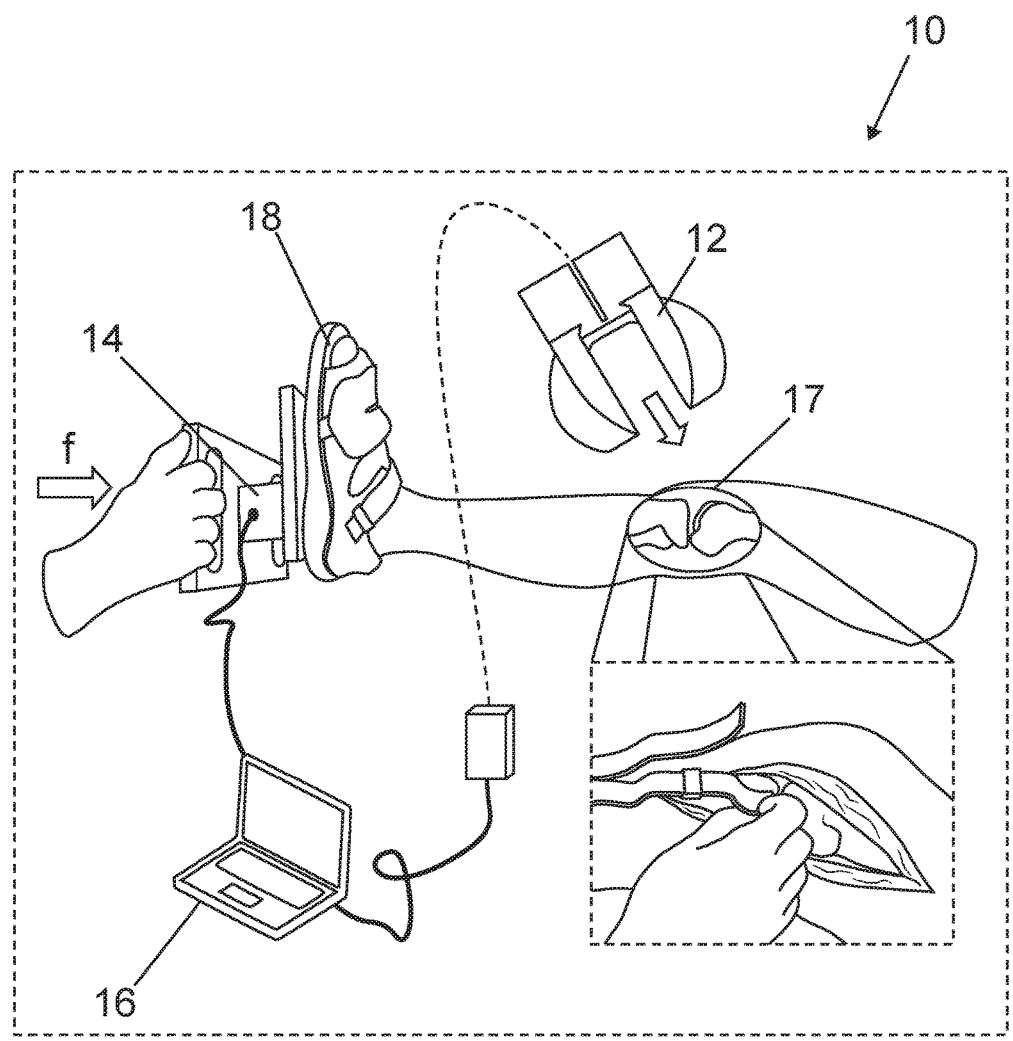
FIG. 1 is a schematic view of a system for intraoperatively measuring joint contact mechanics of a patient's joint in accordance with a preferred embodiment of the present invention.

Reference will now be made in detail to the preferred embodiments of the invention illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as top, bottom, above, below and diagonal, are used with respect to the accompanying drawings. Such directional terms used in conjunction with the following description of the drawings should not be construed to limit the scope of the invention in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, and ±0.1% from the specified value, as such variations are appropriate.

In according with a preferred embodiment, the present invention provides a method for intraoperatively measuring joint contact mechanics of a patient's joint. The method includes inserting a sensor within a joint of a patient.

Specifically, the sensor is inserted between first and second bones of the joint. The method further includes applying a predetermined force to one of the first and second bones, and measuring contact mechanics e.g., stresses, contact areas, forces and locations of stresses, contact areas and forces, between the first and second bones in response to the applied predetermined force. The predetermined force can be a linear force, a torque or a moment. Alternatively, instead of a predetermined force, a predetermined displacement or translation can be applied to one of the first and second bones.

Preferably, the sensor is positioned within the joint on articular cartilage and/or the meniscus of the joint. Articular cartilage covers the surface of synovial joints, while meniscus sits in synovial joints e.g., the knee and temporomandibular joint.

The method allows for the in vivo measurement of joint contact mechanics during surgery i.e., intraoperatively. Measuring quantitative data on in vivo contact mechanics within the joint would allow the surgeon to gather information about joint mechanics in the injured condition, and then again during and after the surgical intervention. Armed with this information, the surgeon could tailor the surgical technique (use of scaffolds/number of sutures/use of biological augments, amount of tissue resection) to mitigate e.g., unusually high contact stresses. This information would not only help surgeons understand the mechanical consequences of their existing surgical techniques, but also as new techniques or new implants/scaffolds for tissue repair emerge into clinical use, unique information could be gathered that would help evaluate their ability to restore acceptable contact mechanics to the affected joint. Finally, in a broader, population based study, the data generated from such intraoperative measures, would provide valuable insight into the mechanisms for the continued joint degeneration after joint injuries and surgical treatments. The system could also be used in veterinary medicine, both in the treatment of patients, or in animal models intended to be used as a screening for new technologies.

The direct, intraoperative measurement of joint contact mechanics can provide useful information about the mechanical condition of the injured joint, the mechanical condition of the joint during the trial placement of a device intended to replace the joint, the mechanical condition of the joint during a surgery intended to repair an injured tissue, and the mechanical condition of the joint at the end of the surgery.

This information can be used to make adjustments at the time of surgery for implant placement (for example, when assessed at the trial implantation stage of a total knee replacement or the positioning of meniscal allografts), to the tightening of ligaments that span the joint (e.g., when ligament loosening procedures are done during joint replacement), and to give feedback to the surgical team about the mechanical condition of the joint immediately after intervention. Such information may advantageously be predictive of short term or long term outcome and that the data generated may help identify patients that should be targeted in the primary prevention of osteoarthritis.

The method for measuring intraoperative joint contact mechanics is preferably accomplished with a system 10 (FIG. 1) to enable joint contact mechanics (e.g., joint contact stress, contact area and forces) to be quantified in an operative environment, under controlled loads. The system 10 for measuring intraoperative joint contact mechanics of a patient's joint includes a sensor 12, a load cell 14, and a computer 16. The sensor measures joint contact mechanics between first and second bones 17 of the joint. The load cell measures and records forces and/or moments applied to one of the first and second bones of the joint. The computer is operatively in communication with the load cell and sensor, and configured to record contact mechanics data e.g., contact stresses and contact areas, measured by the sensor upon application of forces which are measured by the load cell.

The sensor 12 is preferably a thin high-resolution sensor capable of quantifying contact mechanics. Preferably, the sensor is a thin sensor that can measure contact stresses, contact areas, forces and the locations of the contact stresses, contact areas and forces, such as a pressure mapping sensor. The sensor is preferably a thin sensor that can be easily sterilized, and which can be easily inserted between the articular surfaces without significantly altering the native joint structure. The sensor can either be inserted flat through an arthrotomy, or 'rolled' to facilitate insertion through a cannula for arthroscopic surgery, as further discussed below.

Figure 4:
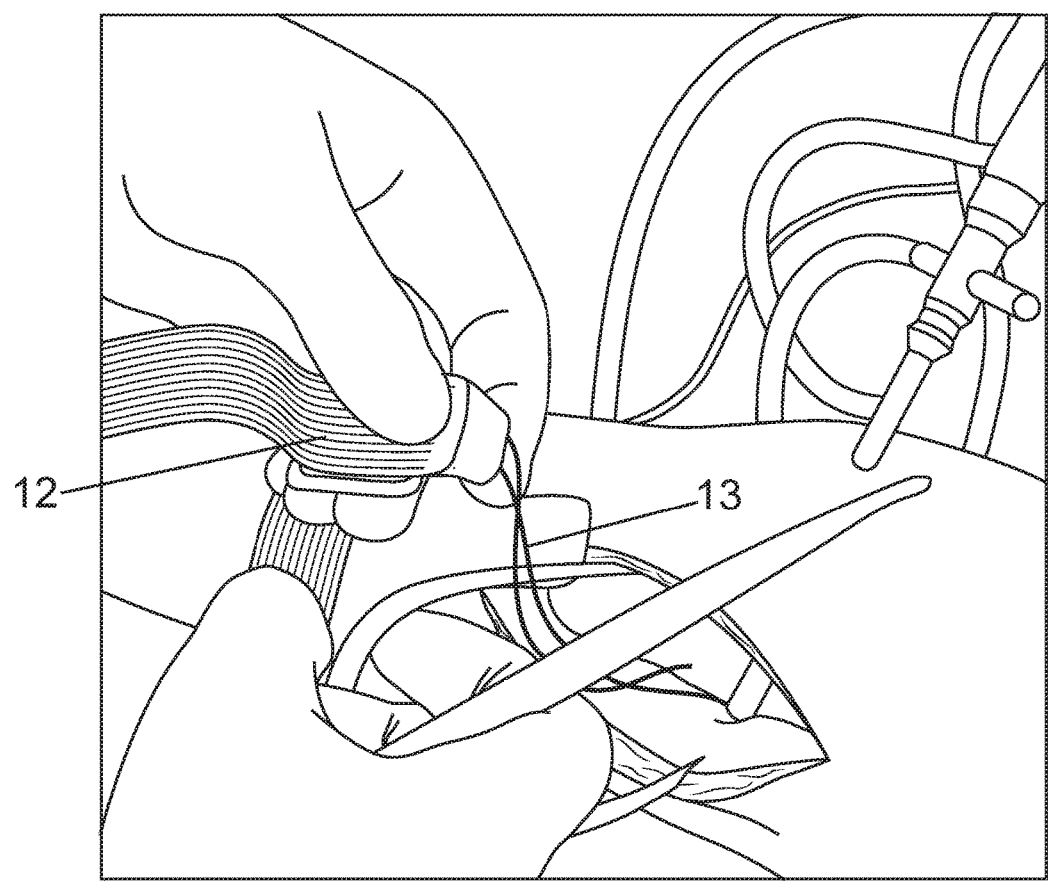
FIG. 4 is an enlarged perspective view of a sensor of the system for intraoperatively measuring joint contact mechanics of FIG. 1.
Figure 5A:
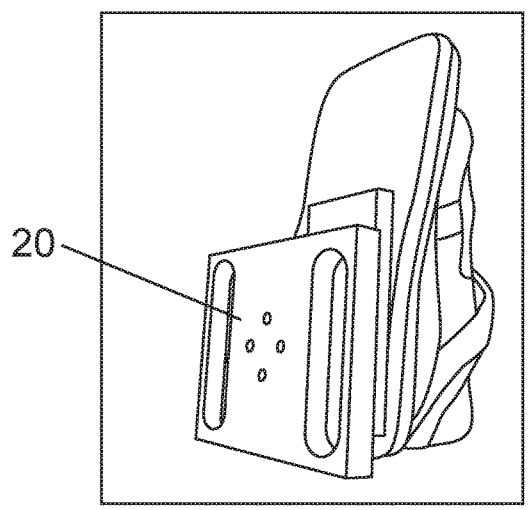
FIGS. 5A-5D are various views of a surgical boot having a load cell in accordance with a preferred embodiment of the present invention.
Figure 5B:
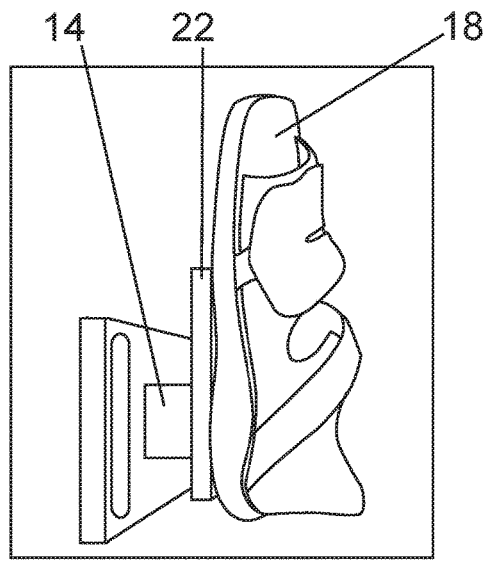
Figure 5C:
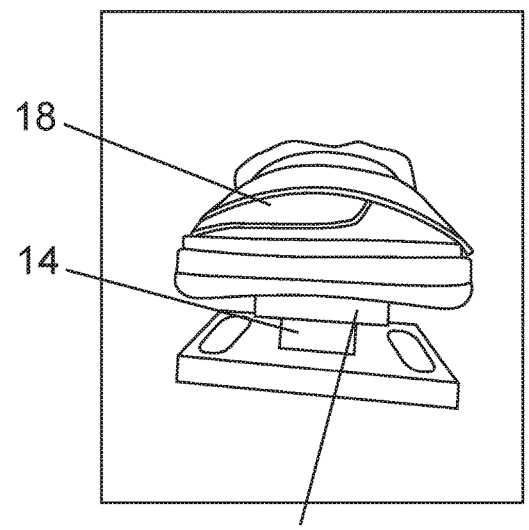
Figure 5D:
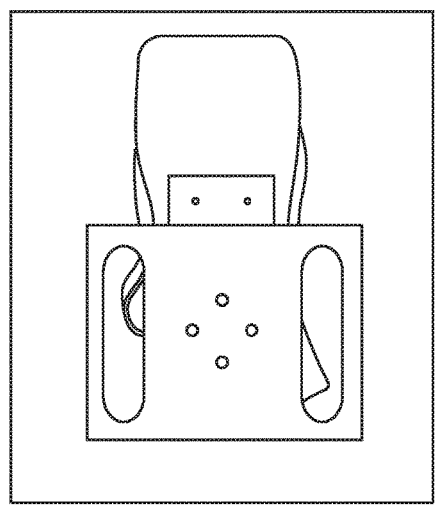

The sensor 12 is capable of measuring contact mechanics. Sensors applicable to the present invention include, for example, I-Scan of Tekscan Inc., MA, and Intra-articular Kneepad of Novel Inc., MN. Prior to use the sensor is sterilized, preferably using Ethylene Oxide (ETO) after several small holes are created on the tabs to enable the insertion of sutures 13 at the time of surgery (FIG. 4). However, alternative sterilization methods can also be used to sterilize the sensor, such as supercritical carbon dioxide sterilization, gamma sterilization, and steam sterilization.

One or more sensors 12 is placed in the joint between first and second bones of the joint, preferably under the menisci, but on top of the articular cartilage. The sensors are used to measure the distribution of force across the joint (peak contact force, contact area, distribution of force). The sensor is detachable from the computer so as to allow for individualized sterilization.

Alternatively, the sensor 12 can be placed between a tendon and a bone to measure contact stresses and contact areas between the tendon and bone. For example, the sensor can be placed between the rotator cuff tendon and the overlying acromion for measuring contact between the two. Further, the sensor can be placed between a meniscus and an underlying bone to measure contact area and contact stresses between the meniscus and underlying bone. Furthermore, the sensor can be placed between cartilage and bone of a joint to measure contact area and contact stresses between the cartilage and bone.

Figure 2A:
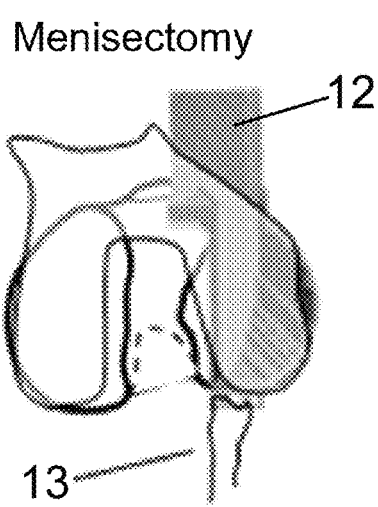
FIGS. 2A-2D are illustrations of sensor placement within a knee joint and contact stresses measured within a knee joint in accordance with an exemplary method of intraoperatively measuring joint contact mechanics of a knee joint.
Figure 2B:
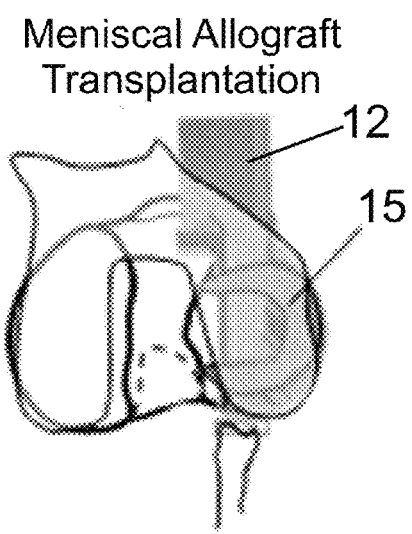
Figure 2C:
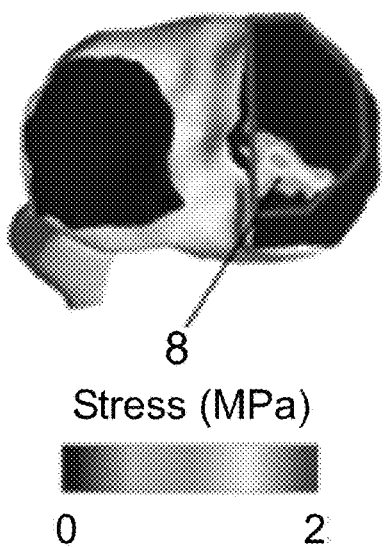
Figure 2D:
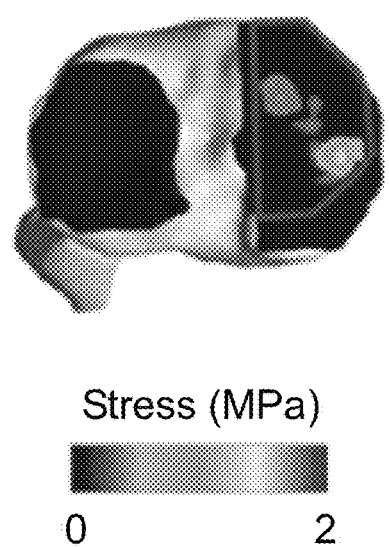

In an exemplary application, FIGS. 2A and 4 illustrate the sensor 12 attached or being attached to soft tissue adjacent a femur with a suture 13. FIG. 2B illustrates the positioning of a meniscal allograft 15 relative to the sensor 12. FIGS. 2C and 2D illustrate representative contact stress maps obtained by the sensor with respect to a knee joint before and after meniscal allograft transplantation.

Figure 15:
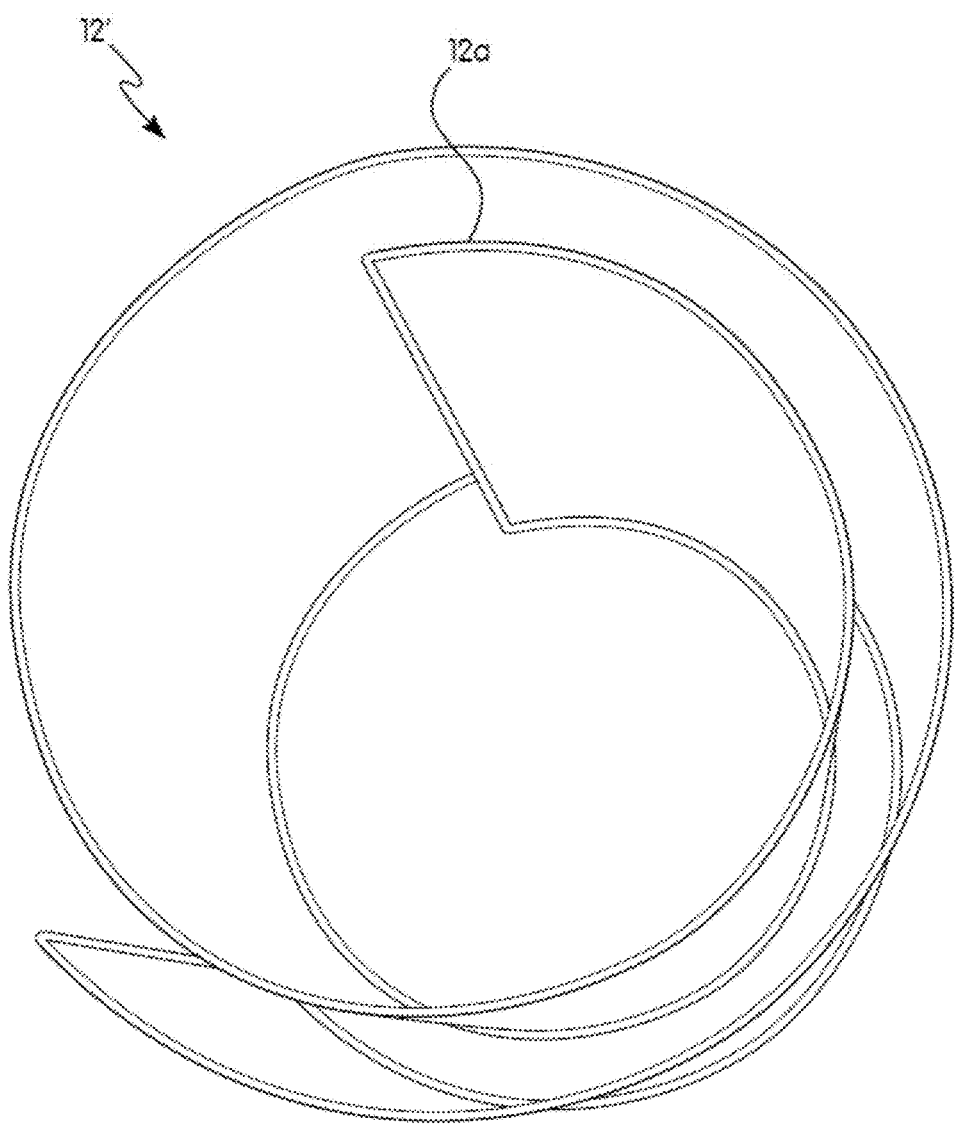
FIG. 15 is a perspective view of a sensor in a rolled configuration in accordance with a preferred embodiment of the system for intraoperatively measuring joint contact mechanics of a patient's joint.

In accordance with another aspect of the present invention, the sensor 12' (FIG. 15) is rolled to allow insertion of the sensor through a cannula for arthroscopic surgery. In this aspect, the sensor 12' is formed, in part, from shape memory alloy e.g., via a rim 12a or throughout the sensor, so as to retain a substantially planar or unrolled form. As such, after the sensor is rolled and inserted into the joint via the cannula, the sensor 12' is unfolded to its substantially planar form. Shape memory alloys applicable to the present invention are disclosed for example in U.S. Pat. No. 8,555,633, the entire disclosure of which is hereby incorporated by reference in its entirety for all purposes. In sum, the sensor is rolled into a rolled configuration and then inserted into a cannula of an arthroscopic instrument. The cannula is then inserted into the patient's joint and then the rolled sensor is ejected from the cannula into the joint. Thereafter, the rolled sensor is unrolled into its substantially planar form.

Figure 3:
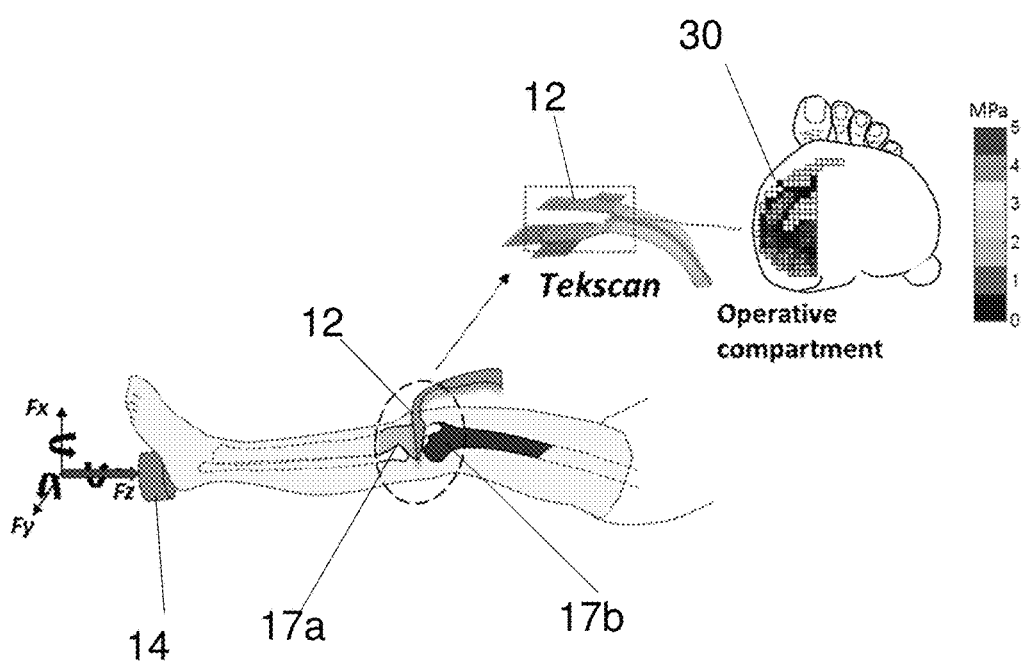
FIG. 3 is a schematic illustration of a sensor of the system of FIG. 1 applied to a knee joint and a data map of measured contact stresses.

FIG. 3 is a schematic illustration of the system and method of the present embodiment. The placement of a sensor (e.g., a Tekscan sensor or Pliance Sensors of Novel MN, USA) is inserted between the tibia 17a and femur 17b of a patient's knee joint. The sensor is placed under the meniscus and across the tibial plateau. The sensor can output a map 30 e.g., of the contact stresses across the tibial plateau in the operated compartment. An instrumented boot 18, as further discussed below, is placed against the foot. The surgeon pushes against the boot with a controlled and recorded force and a load cell 14 in the boot quantifies the forces applied. In this way, the contact mechanics across the tibial plateau for a known force are computed.

The load cell 14 is preferably constructed in combination with a lightweight device for mounting the load cell thereto and which can be placed against the joint so that a surgeon can push with a known force or torque across the joint of interest. The device could also be augmented with a goniometer to record translations or rotations, or augmented with surgical navigation 100, so that more assessment of joint forces in response to the applied forces or displacements can be conducted.

In the current embodiment, the forces/displacements are applied manually, however, the lightweight device could be mechanized to automate the process of applying controlled forces and displacements. The load cell can be a uniaxial or multi-axis load cell.

Figure 6:
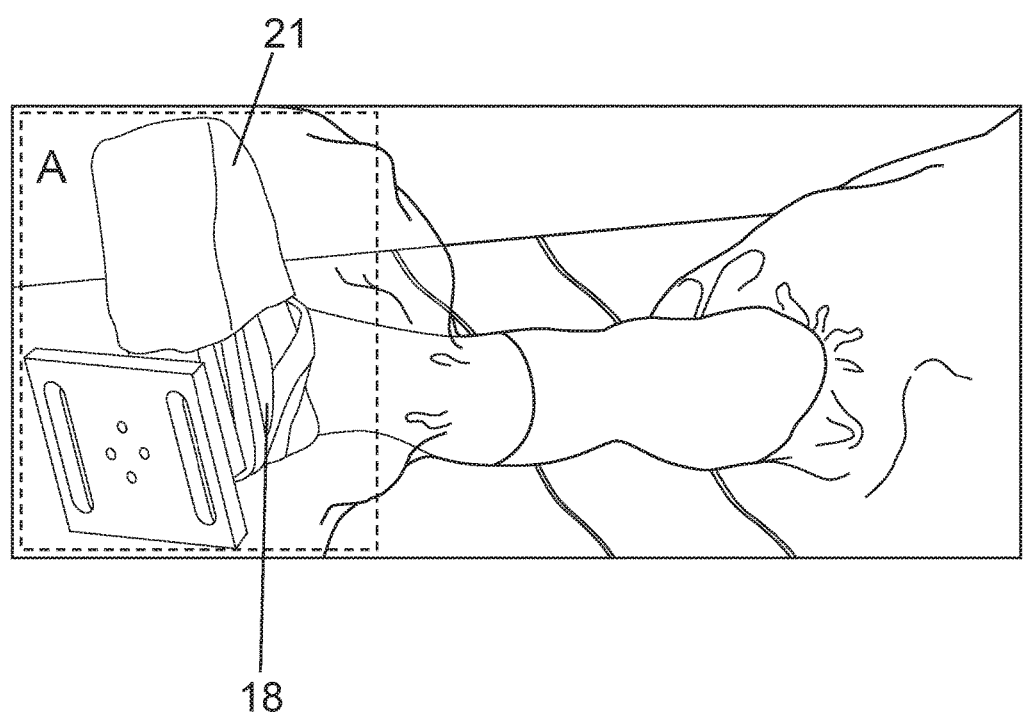
FIG. 6 is a perspective view the surgical boot of FIGS. 5A-5D wrapped in a protective cover.

Referring to FIGS. 1, 4, 5A-5D and 7A-7E, an exemplary light weight device applicable to the knee joint can be configured as a surgical shoe 18. The surgical shoe is mounted onto the load cell 14 and equipped with a handle 20 placed on and attached to the foot of the surgical shoe. The load cell and shoe are non-sterile, thus they can be covered with e.g., a sterile C-Arm drape 21 (FIG. 6). The surgical shoe 18 is attached to an aluminum force plate 22. The load cell 14 is sandwiched between the force plate and the handle which can be made of Delrin. The load cell can be designed so that it can be readily detached from the handle and the shoe, therefore, different load cells can be used for different cases.

Figures 7A, 7B, 7C:
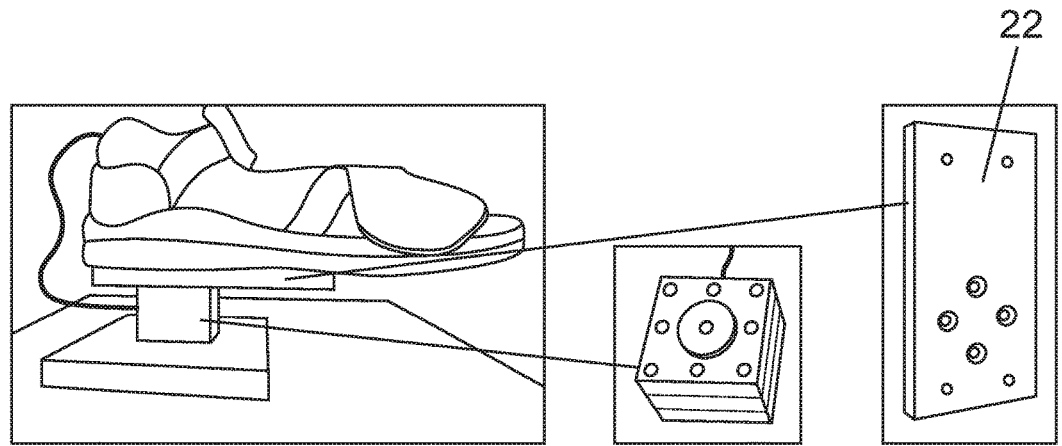
FIGS. 7A-7E are various views of another surgical boot having a load cell in accordance with a preferred embodiment of the present invention.
Figure 7D:
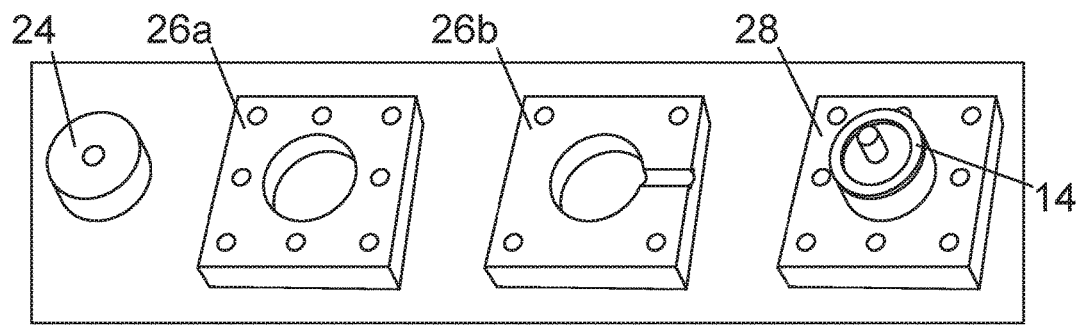
Figure 7E:
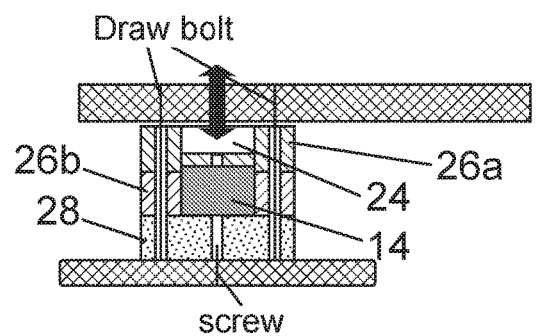

FIGS. 5A-5D illustrate the surgical shoe 18. FIG. 7A illustrates the surgical shoe in a fully assembled state. FIG. 7D illustrates the following components forming the surgical shoe, an aluminum disk 24 with one end for contact with the force plate and the other end for connection to the load cell, spacers 26a, 26b each having four through holes for the installation of bolts, an aluminum base 28 which attaches to the load cell and has four threaded holes for connecting to the handle, and the load cell 14. FIG. 7B illustrates the aluminum disk, spacers, aluminum base and load cell in an assembled state. FIG. 7C illustrates the force plate 22. FIG. 7E is a schematic view of an assembly of the load cell, disk, spacers and base.

Figure 8:
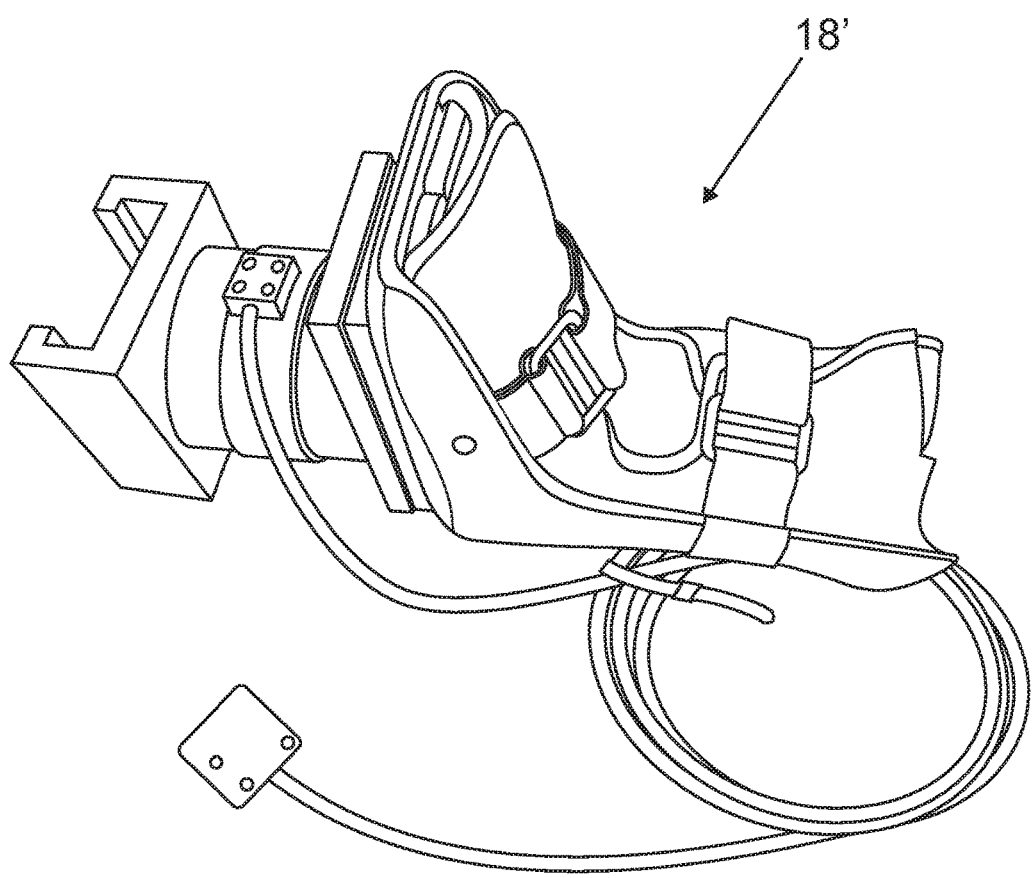
FIG. 8 is a perspective view of yet another surgical boot having a load cell in accordance with a preferred embodiment of the present invention.

FIG. 8 illustrates another embodiment of the surgical boot 18' having similar components as surgical boot 18.

Referring to FIG. 1, the computer 16 includes data acquisition software to record the applied load and resulting joint contact mechanics, outside of the sterile space. The computer can be hard-wired to the load cell and sensors or operatively connected via wireless connections.

Analog signals from the load cell are preferably collected by the computer via a data acquisition card, such as USB 6008 of National Instruments Inc. A graphic user interface (e.g., Matlab 2012 of Mathworks, Natick, Mass.) is configured to monitor and record the applied force in real-time (e.g., up to 50 Hz). The applied forces from the load cell and the intra-articular contact stresses from the sensor are then synchronously collected.

Figure 10:
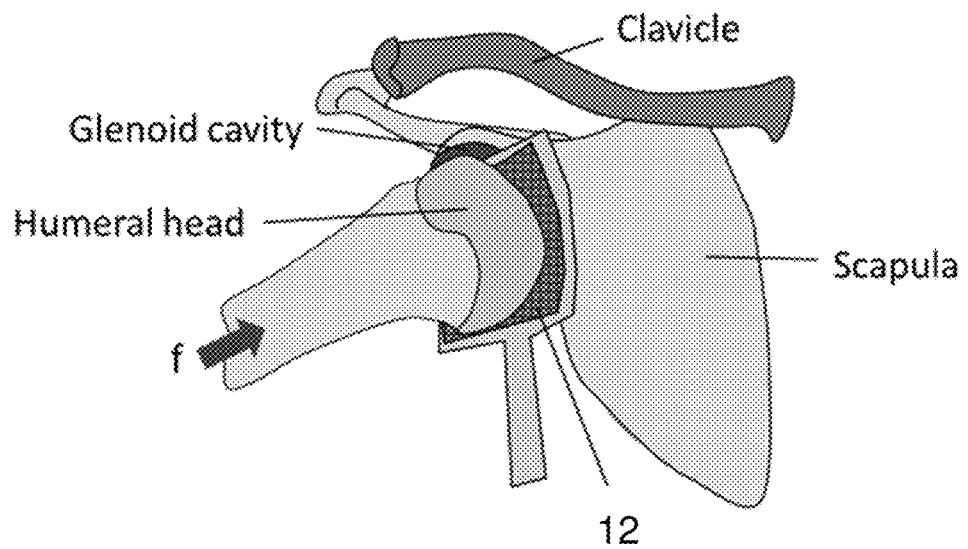
FIG. 10 is a schematic partial perspective view of the system for intraoperatively measuring joint contact mechanics applied to a shoulder joint.

FIG. 1 illustrates the system 10 for measuring intraoperative joint contact mechanics of a patient's joint configured for application to a knee joint. However, the system 10 can alternatively be configured and applied to other anatomical joints, such as the shoulder (FIG. 10), hip, elbow and ankle.

The system 10 provides real-time measurement of in vivo joint contact mechanics including contact stresses, contact area and forces e.g., total force (acting across the surface of a joint) under known loads that can be quantified intraoperatively at various stages or times throughout the surgery.

Figure 9:
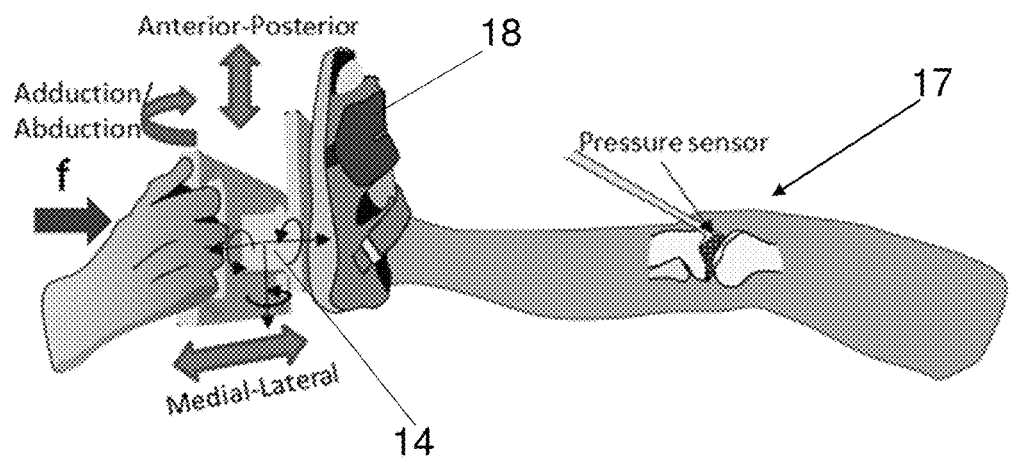
FIG. 9 is a schematic view of the system for intraoperatively measuring joint contact mechanics applied to a knee joint of a patient.

The system 10 can be used to apply an axial force, however, it could also be used to apply a torque. Referring to FIG. 9, by using a 6-axis load cell, the system can be used to record the forces and moments applied in other directions with or without concurrent axial load. Therefore, the knee joint contact mechanics under various joint alignments or loading scenarios can be evaluated. In addition to the knee joint, this device can also be used to measure the contact mechanics in other joints, such as the shoulder or hip by using a sensor with applicable geometry.

In accordance with another aspect of the present invention, there is provided a surgical navigation system 100 (FIG. 11) configured to track the first and second bones 17 of a joint e.g., a tibia 17a and a femur 17b upon application of forces by the load cell. To precisely control the joint position and alignment during force application, the system 10 can be used in combination with the surgical navigation system 100. Briefly, rigid pins with multiple retro-reflective optical markers could be attached to the proximal and distal segments of the joint. Thus, cameras could track the 3D coordinates of the markers to calculate joint rotation and translation of the first and second bones under the applied forces/moments/displacements. Such surgical navigation systems are known in the art. However, surgical navigation systems applicable to the present invention include U.S. Pat. Nos. 7,139,601; 7,366,562; 7,751,865; 8,623,030; 8,644,907, and 9,082,319 the entire discloses of which are hereby incorporated by reference herein for all purposes.

EXAMPLE I

The foregoing system and method for measuring joint contact mechanics were evaluated by measuring the in vivo knee joint contact stresses in patients before and after meniscal allograft transplantation in five patients.

Patient Enrollment:

Seven patients (4 Male/3 Female, age 22.3±6.6 yrs, weight 73.8±12.1 kg, height 1.70±0.82 m) who were undergoing meniscal allograft transplantation (2 medial, 5 lateral) were enrolled in this study. Two had concomitant anterior cruciate ligament reconstruction, and three had osteochondral allograft transplantation. All patients had undergone prior total meniscectomy.

Sensor Calibration and Sterilization:

A thin electronic pressure sensor (model: 4011, Tekscan Inc.) was equilibrated (15 psi and 30 psi) using an air filled bladder and calibrated (0 N, 500 N and 2400 N) using an MTS machine following standard procedure. The edge of the sensor was trimmed to accommodate the shape of the tibial plateau. Three 0.9 mm pre-drilled holes were created on the posterior tab for subsequent suture placement. The sensor was double pouched using High Temperature & ETO Sterilization Tubing (STERIS) and underwent sterilization using ethylene oxide. The sensor was re-calibrated following surgery to correct the potential sensitivity drift due to sterilization. A custom designed surgical boot was used to manually apply an axial load to the foot intraoperatively for contact stress measurement. The boot was equipped with a load cell (Model: 31/1432-04, Honeywell Inc.) to monitor the applied load in real-time. The surgical shoe was covered with a sterile C-Arm drape.

Data Collection:

After arthroscopic debridement of the involved compartment, the sensor was passed through a small arthrotomy from anterior to posterior by pulling the posterior tab via a passing suture placed through a posterolateral or posteromedial incision, and its position was adjusted arthroscopically to cover the weight bearing region of the tibial plateau. The anterior edge of the sensor was aligned flush with the tibial plateau edge which was used for position registration of the sensor. The sensor was secured in place with suture and an axial load was applied with the knee in full extension. The thigh and lower leg were stabilized to minimize joint axial rotation and tilting during load application. The externally applied load and joint contact stress were synchronously recorded. Three trials were collected with the load ramping from 0 to 50% body weight. The sensor was removed after data collection. Meniscal allograft was then inserted into the joint and reduced to the proper position with rigid fixation at both horn attachments. After graft placement, the sensor was re-inserted, secured underneath the graft, and data collection was repeated. Pre-operative morphological MRI scans (3D-SPGR) were also acquired to reconstruct the knee joint geometries.

Data Analysis:

The peak contact stress and contact area on the tibial plateau under a joint load equal to 50% body weight were calculated for the meniscectomy and meniscal transplanted conditions. MR images were manually segmented to create 3D models of articular cartilage and bone. A model of the sensor was created with its anterior edge aligned with the tibial plateau edge to determine the location of contact stress on the tibial plateau (FIG. 12A). Peak contact stress and contact area were compared between meniscectomy and meniscal transplanted conditions using a paired t-test. FIGS. 12B and 12C show arthroscopic views of the sensor 12 positioned within a knee joint between a tibia and femur.

Figure 13A:
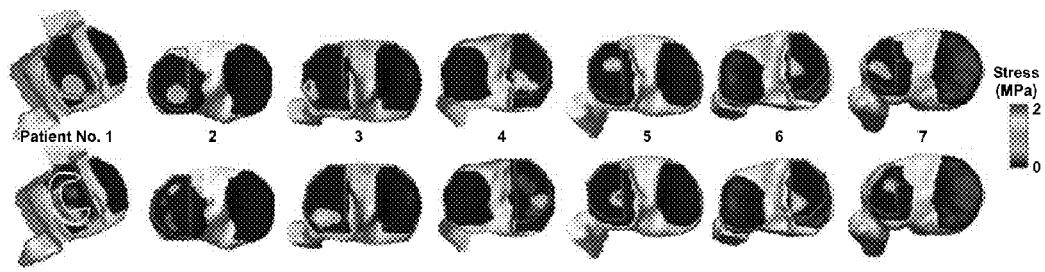
FIG. 13A are contact stress maps on the tibial plateau before (1st row) and after (2nd row) graft placement.
Figure 13B:
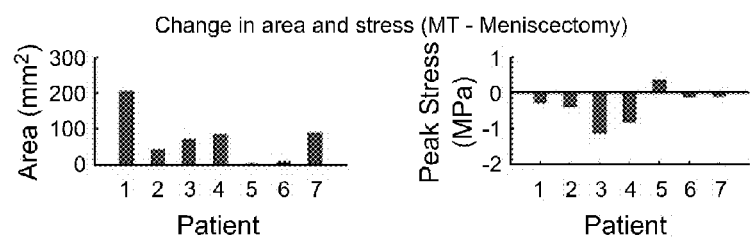
FIG. 13B are graphs illustrating measured contact areas and peak stresses of Example I.

Results:

Meniscal allograft transplantation resulted in a decrease in peak contact stress as compared to the meniscectomy, 1.40±0.53 MPa vs. 1.74±0.49 MPa, but was not significant, p=0.11. A significant increase in contact area was detected, 248±98 $mm^2$ vs. 178±49.4 $mm^2$, p=0.04 (FIG. 13B). In addition, posterior shift of contact centroid following meniscal allograft transplantation was noted, especially for patient 5, where a posterior shift was observed coupling with an increase in the stress which may be attributed to patient specific morphology of the articular surface. The stress maps varied greatly among these 7 patients (FIG. 13A). Three patients (Nos. 1, 2, 7) displayed partial restoration of the C-shape footprint underneath the meniscus following meniscal allograft transplantation, but this was not evident in other patients. With respect to the knee joint, the C-shaped, wedge-like menisci function to distribute loads across articular cartilage that covers what, without the menisci, would otherwise be an incongruent joint.

This evaluation exemplifies the data obtainable using the present method and system for intraoperatively measuring joint contact mechanics to measure in vivo knee joint contact mechanics during meniscal transplantation surgery. Decreased peak contact stress and increased contact area provides biomechanical evidence of a positive effect of meniscal allograft transplantation on patients with meniscal deficiency. The subject-specific characteristics in stress mappings sheds light on the variant long-term outcomes following meniscal allograft transplantation. Further, the foregoing data shows that specific articular surface geometry may need to be considered in surgical planning.

EXAMPLE II

Other forces and torques were measured across a knee joint of a patient using the system for intraoperatively measuring joint contact mechanics discussed above. A 6-axis load cell was used to measure and record applied forces and torques other than axial forces. The applied forces were: ap—anterior-posterior, ml—medial-lateral, and si—superior-inferior; and the applied torques were: fe—flexion/extension, ie—internal/external, and vv—varus/valgus.

Figure 14A:
FIGS. 14A-14C are data maps and graphs of data collected from Example II.
Figure 14B:
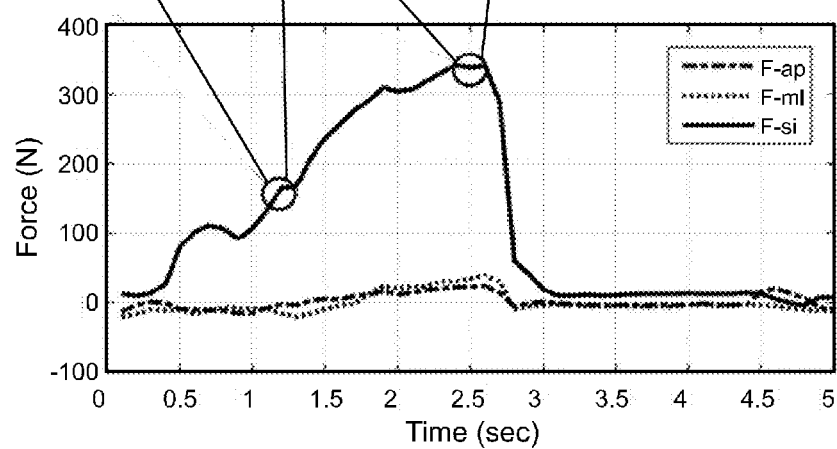
Figure 14C:
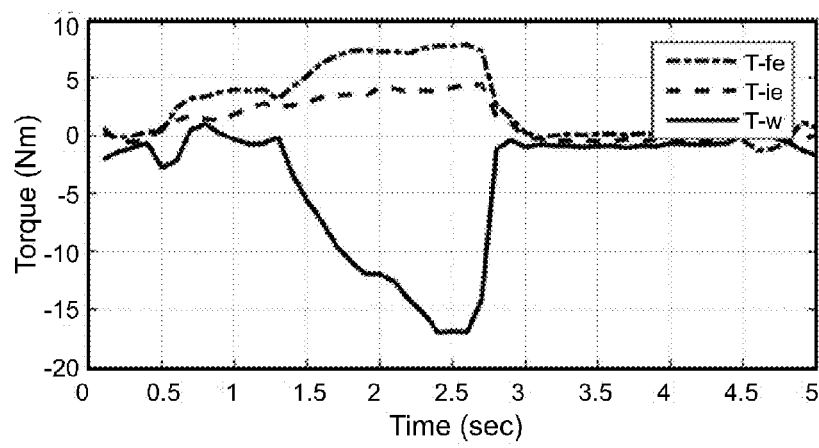

FIG. 14A shows the contact stress map of this Example. FIGS. 14B and 14C illustrate graphs of Force v. Time and Torque v. Time for this Example.

It will be appreciated by those skilled in the art that changes could be made to the embodiments described above without departing from the broad inventive concept thereof. It is to be understood, therefore, that this invention is not limited to the particular preferred embodiments disclosed, but it is intended to cover modifications within the spirit and scope of the present invention as defined by the appended claims.

We claim:

1. A method for intraoperatively measuring joint contact mechanics of a patient's joint comprising:
   inserting a sensor between first and second bones of a joint;
   applying a predetermined force to one of the first and second bones;
   using a load cell, measuring the applied predetermined force; and
   using the sensor, measuring contact mechanics between the first and second bones in response to the applied predetermined force.

2. The method of claim 1, wherein the predetermined force is a linear force, a torque or a moment.

3. The method of claim 1, wherein the step of applying a predetermined force comprises rotating the joint throughout a range of motion, or displacing or translating one of the first and second bones relative to the other of the first and second bones.

4. The method of claim 1, further comprising tracking movement of the first and second bones in response to the applied predetermined force using a surgical navigation system.

5. The method of claim 1, further comprising mitigating joint interaction about areas of measured contact stresses or contact areas.

6. The method of claim 5, wherein the mitigating step comprises applying scaffolds, sutures, biological augments, or tissue resection to one of the first and second bones.

7. The method of claim 5, wherein the mitigating step comprises replacing or resurfacing the joint with an orthopedic implant.

8. The method of claim 1, wherein the measuring step comprises intraoperatively measuring a plurality of contact mechanics at various times.

9. The method of claim 1, further comprising developing a contact stress map based on the measured contact stresses.

10. The method of claim 1, wherein the measuring step includes measuring the location of a contact area, a contact stress, forces or moments between the first and second bones in response to the applied predetermined force.

11. The method of claim 1, wherein the inserting step comprises inserting the sensor between at least one of a tendon, a cartilage, and a meniscus, and the first bone.

12. The method of claim 1, further comprising:
applying another predetermined force to one of the first and second bones of the joint;
using the load cell, measuring the applied another predetermined force; and
using the sensor, measuring contact mechanics between the first and second bones in response to the applied another predetermined force.

13. A system for intraoperatively measuring joint contact mechanics of a patient's joint comprising:
a sensor for measuring joint contact stresses between first and second bones of the joint;
a load cell spaced from and movable relative to the sensor for measuring forces applied to one of the first and second bones; and
a computer operatively in communication with the sensor and the load cell to record contact mechanics measured by the sensor and applied forces measured by the load cell upon application of forces to one of the first and second bones.

14. The system of claim 13, wherein the sensor includes sutures for securing to soft tissue adjacent one of the first and second bones.

15. The system of claim 13, further comprising a surgical navigation system configured to track the first and second bones upon application of forces to the first and second bones.

16. The system of claim 13, wherein the sensor comprises shape memory alloy.

17. The system of claim 13, further comprising an instrumented surgical mount that includes:
a fastener for attaching to a patient;
the load cell mounted to the fastener;
a force plate mounted between the fastener and the load cell; and
a handle assembly attachable to the load cell.

18. A method for intraoperatively measuring joint contact mechanics of a patient's joint comprising:
inserting a sensor between first and second bones of a joint and suturing the sensor to soft tissue adjacent one of the first and second bones;
applying a predetermined force to one of the first and second bones; and
measuring contact mechanics between the first and second bones in response to the applied predetermined force.

19. A method for intraoperatively measuring joint contact mechanics of a patient's joint comprising:
inserting a sensor between first and second bones of a joint by rolling the sensor into a rolled configuration, inserting the rolled sensor into a cannula, inserting the cannula into the joint, and unrolling the sensor within the joint;
applying a predetermined force to one of the first and second bones; and
measuring contact mechanics between the first and second bones in response to the applied predetermined force.

* * * * *